United States Patent [19]

Beaudet

[11] 3,976,646

[45] Aug. 24, 1976

[54] PROCESS FOR PREPARING EQUIMOLECULAR SALT OF PIPERAZINE AND 1,2-DIPHENYL-4-BUTYL-3,5-DIOXO PYRAZOLIDINE

[75] Inventor: Camille Beaudet, Brussels, Belgium

[73] Assignee: Societe d'Etudes et de Realisations Scientifiques en Abrege, Brussels, Belgium

[22] Filed: Nov. 20, 1974

[21] Appl. No.: 525,709

Related U.S. Application Data

[63] Continuation-in-part of Ser. No. 260,950, June 8, 1972, abandoned.

[30] Foreign Application Priority Data

June 10, 1971  United Kingdom............... 19881/71

[52] U.S. Cl........................ 260/268 H; 260/268 R; 424/250
[51] Int. Cl.².............. C07D 403/00; C07D 403/04
[58] Field of Search..................... 260/268 R, 268 H

[56] References Cited

OTHER PUBLICATIONS

Camille Beaudet, Chemical Abstracts, vol. 78, p. 84443t (1973).

*Primary Examiner*—Alton D. Rollins
*Assistant Examiner*—Jose Tovar
*Attorney, Agent, or Firm*—Kaufman & Kramer

[57] ABSTRACT

The equimolecular salt of piperazine and 1,2-diphenyl-4-butyl-3,5-dioxopyrazolidine is prepared by stirring together separately prepared solutions of the two compounds in the same organic solvent, selected among the ketones, ethers, toluene and chlorinated aliphatic hydrocarbons containing 1 to 3 carbon atoms and by seeding the reaction mixture by means of crystals of the equimolecular salt when temperature of the reaction mixture has decreased to a value at which the seeding crystals are not dissolved in said mixture and before any precipitate appears in said reaction mixture.

3 Claims, No Drawings

PROCESS FOR PREPARING EQUIMOLECULAR SALT OF PIPERAZINE AND 1,2-DIPHENYL-4-BUTYL-3,5-DIOXO PYRAZOLIDINE

CROSS REFERENCE TO RELATED APPLICATION

This is a continuation-in-part of copending application Ser. No. 260,950, filed June 8, 1972, now abandoned.

BACKGROUND OF THE INVENTION

1. Field of the Invention

The equimolecular salt of piperazine and 1,2-diphenyl-4-butyl-3,5-dioxo pyrazolidine of the following formula

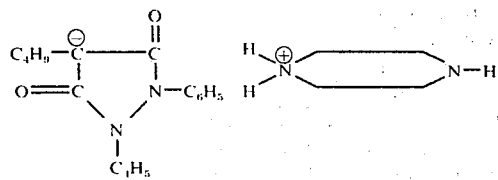

is a known compound which is used as a pharmaceutical compound for the treatment of rheumatic diseases.

This invention relates to an improved method or process for preparing said salt of formula I.

2. Description of Prior Art

According to a known method for preparing said salt of formula I, anhydrous piperazine is dissolved in acetone, the obtained solution is poured into a solution of the pyrazolidine derivative also in acetone, the obtained mixture is poured into hexane, wherein the desired salt precipitates, said precipitate being finally separated by filtration and dried.

In a particular embodiment of said known method 17.4 g of anhydrous piperazine (0.2 mole; excess of 100%) are dissolved in 550 ml of acetone and the obtained solution is poured into a solution of 30.8 g (0.1 mole) of the pyrazolidine derivative in 550 ml of acetone, the obtained mixture being then poured into 1100 mol of hexane, 32 g of the desired salt are obtained.

The yield of the desired salt, when the known method is used, is about 80–82 percent.

SUMMARY OF THE INVENTION

According to this invention, it is possible to obtain the equimolecular salt of piperazine and 1,2-diphenyl-4-butyl-3,5-dioxo-pyrazolidine with -dioxo pyrazolidine much better yield and in more economical way, when a single solvent is selected, wherein the starting reagents are soluble and the desired salt is insoluble and when the precipitation of the equimolecular salt is initiated by adding seeding crystals to the reaction mixture at a proper time.

In the process according to this invention, anhydrous piperazine, preferably in excess, and 1,2-diphenyl-4-butyl-3,5-dioxo pyrazolidine are both separately dissolved in the same organic solvent selected among the ketones, ethers, toluene and chlorinated aliphatic hydrocarbons of the general formula:

$C_x H_y Cl_z$ (II)

in which $x = 1$, 2 or 3, $y = 0$ to 6 inclusive and $z = 1$ to 6 inclusive, the solution of 1,2-diphenyl-4-butyl-3,5-dioxo pyrazolidine is added to the solution of piperazine, the obtained mixture is stirred at about 20°–35°C or at the boiling point of the solvent and some seed crystals are added to the reaction mixture before any precipitate appears in it and when the temperature of this reaction mixture is low enough so that the seeding crystals do not become dissolved in said mixture, the mixture being then stirred until a precipitate of the desired salt is obtained, said precipitate being finally separated by filtration, washed and dried.

It has been found that the addition of seed crystals of the equimolecular salt to the reaction mixture must take place during a critical time interval.

It has been found that, when the mixture of the two solutions containing respectively 1,2-diphenyl-4-butyl-3,5-dioxo pyrazolidine and piperazine are mixed and stirred, the temperature of the mixture increases and may reach a value at which seeding crystals of the equimolecular salt, when added thereto, become dissolved in said mixture.

When this occurs, i.e. when the seed crystals added to the reaction mixture become dissolved therein, it has been found that a mixture of the equimolecular salt and of a double salt precipitates in the reaction mixture.

It has also been found that, when no seed crystals of the equimolecular salt are added to the reaction mixture or when such seeding crystals are added to said mixture too late, i.e. when a precipitation has begun, a mixture of the desired equimolecular salt and of a double salt is also obtained.

The amount of double salt obtained together with the desired equimolecular salt in the precipitate may be of about 20% by weight, when the seed crystals of the equimolecular salt are not added to the reaction mixture during the critical time interval.

The double salt of 1,2-diphenyl-4-butyl-3,5-dioxo pyrazolidine and piperazine contains two moles of the first compound and 1 mole of the second compound. This double salt may be represented by the following formula:

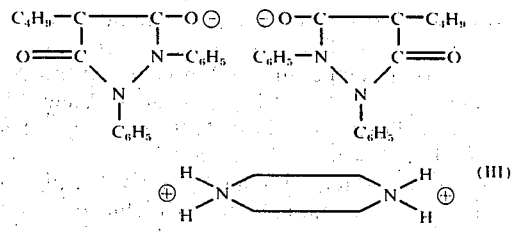

The double salt of the formula III is inactive, this salt having no acute toxicity by oral route on rats, since the administration of 1 g/kg of said salt to rats has no effect.

On the contrary the equimolecular salt of formula I prepared by the process according to this invention is active and is more than 3.3 times less toxic than phenylbutazone.

DETAILED DESCRIPTION OF THE INVENTION

Among the solvents which may be used acetone, dioxane, tetrahydrofuran, toluene, chloroform ($CHCl_3$), carbon tetrachloride, ($CCl_4$), dichloromethane dichloro-1,1-ethane (CH$_3$—CHCl$_2$) and dichloro-1,2-ethane (CH$_2$Cl—CH$_2$Cl) are preferred.

The precipitate of the desired salt is preferably washed with hexane or light petroleum ether and dried at room temperature or about 50°C.

According to a feature of this invention, an excess of piperazine, preferably an excess of 5 to 20% in respect of the stoechiometric amount, is used.

Said excess of piperazine still dissolved in the used solvent can be recovered in the filtrate resulting from the filtration of the precipitate of the desired salt.

After concentration of said filtrate by removing the excess of solvent (which may be used for dissolving a fresh quantity of the pyrazolidine derivative) a suitable amount of piperazine may be added to the concentrated filtrate so as to obtain again a solution of piperazine in the solvent, said solution being mixed with a solution of the pyrazolidine derivative in the same solvent for preparing a further amount of the desired salt.

The solvent used for the preparation of a certain amount of the desired salt may be recovered by filtration of the precipitate of said salt and used again partly for dissolving a new fraction of piperazine and a new fraction of the pyrazolidine derivative, so as to enable the preparation of a further amount of said salt.

EXAMPLES

The following examples illustrate the method according to this invention.

EXAMPLE 1

To a solution of 17.4 grams (0.2 M; excess of 100%) of piperazine in 300 milliliters of dichloro-1,2-ethane at about 30°–35°C, a solution of 30.8 grams (0.1 M) of 1,2-diphenyl-4-butyl-3,5dioxo pyrazolidine in 500 milliliters of dichloro-1,2-ethane at the same temperature is added.

The reaction mixture is stirred and the temperature of this mixture raises to a value of 42°–45°C. After 15 minutes, there is no further increase of the temperature of the reaction mixture. 1 g of seed crystals of the desired product is added to the reaction mixture when the temperature of this mixture is at about 35°C, so as to initiate the precipitation of said product. The reaction mixture is then stirred during two hours, the crystals are separated by filtration, washed with hexane and dried at room temperature, 38.6 grams of the desired salt melting at 137°–138°C are obtained Yield: 98%).

Analysis: Piperazine: 21.8–21.9% (theory: 21.83%) Pyrazolidine derivative: 78.1–78.2% (theory: 78.17%).

The filtrate which contains 8.7 grams of piperazine dissolved in about 800 milliliters of dichloro-1,2-ethane is concentrated so as to obtain a solution of piperazine in 300 milliliters of dichloro-1,2-ethane. 8.7 grams of piperazine are added to said concentrated filtrate.

On the other hand, 30.8 grams of the pyrazolidine derivative are dissolved in the 500 ml of dichloro-1,2-ethane recovered during the concentration of the above filtrate.

The newly obtained solutions of the two reactants are then mixed and treated as described hereabove, so as to obtain a further amount of the desired salt.

When the process described hereabove is repeated, except that no seed crystals are added to the reaction mixture, a precipitate appears only in this mixture when the temperature thereof is of about 20°C. In this case, the precipitate contains about 80 percent of the desired equimolecular salt and about 20 percent of the inactive double salt.

When the process described above is repeated, except that seed crystals of the desired equimolecular salt are added to the reaction mixture during the time interval where the temperature of the reaction mixture increases from 30°–35°C to 42°–45°C, the seed crystals become dissolved in said mixture and a precipitate appears only in the reaction mixture when the temperature thereof is at about 20°C. In this case also, a mixture of the desired equimolecular salt and of the undesired double salt is obtained.

EXAMPLE 2

A solution of 1,2-diphenyl-4-butyl-3,5-dioxo pyrazolidine (381.5 g) in dioxane (1.9 l) at about 50°C is added to a solution of anhydrous piperazine (115 g) in dioxane (1.9 l) at the same temperature. The mixture is stirred. The temperature of the reaction mixture initially increases to a value of about 55°C and then decreases. When the temperature of the stirred mixture is at 30°–35°C, said mixture is seeded with 1 g of crystals of the desired product. Stirring is continued for 2 hours. The fine crystals are collected by filtration, washed with 300 ml of light petroleum ether and dried at room temperature, 465 g of salt are obtained as pure compound (Yield: 94%) Melting point: 136°–137°C.

Piperazine: 21.8% (calc.: 21.83%).

When the process described hereabove is repeated except that no seed crystals are added to the reaction mixture or seed crystals are added thereto when the temperature of this mixture is at about 55°C, a mixture of the desired equimolecular salt and of the double salt is obtained.

EXAMPLE 3

A boiling solution of 1,2-diphenyl-4-butyl-3,5-dioxo pyrazolidine (308 g) in acetone (300 ml) is added to a boiling solution of piperazine (107.5 g) in acetone (500 ml). The mixture is concentrated to 700 ml and cooled to room temperature. Seeding is then achieved by 1 g of the desired product. The mixture is cooled to −15°C and stirred for two hours.

The crystals are collected on a filter, washed with 250 ml of acetone and dried at room temperature. 373 g of pure desired equimolecular salt are obtained. (Yield: 95%).

When seed crystals of the desired salt are added to the reaction mixture at about 60°C, instead of being added to said mixture when it is at room temperature, the obtained product contains more than 15 percent of impurity (double salt).

On the other hand, when seed crystals are added to the reaction mixture, when this mixture has been cooled to about 10°C, the obtained product also contains a significant amount of double salt.

EXAMPLE 4

To a solution of 13.05 g of anhydrous piperazine in 260 ml of toluene at 50°C, a solution of 43.5 g of 1,2-diphenyl-4-butyl-3,5-dioxo pyrazolidine in 150 ml of toluene also at 50°C is added, while stirring.

The temperature of the reaction mixture first increases to a value of about 55°C and then decreases. When the temperature of the stirred reaction mixture is at about 35°C, seed crystals (1 g) of pure equimolecular salt are added thereto and the mixture is then cooled to room temperature. After filtration, the obtained crystals are washed with toluene and dried under a pressure of 20–30 Torr.

53 g of pure equimolecular salt are obtained (Yield: 94%).

When no seed crystals are added to the reaction mixture or when such crystals are added thereto either at a temperature of more than about 40°C (at which the crystals become dissolved in the reaction mixture) or at room temperature, the obtained product contains a proportion of undesired double salt from 10 to 20 percent by weight.

The method according to this invention has several important advantages when compared to the above described known method:

1. a single solvent is used, wherein the reactants are soluble and the desired salt is insoluble;
2. the yield of the desired salt (more than 90 percent) is far better than the yield obtained with the known process (80–82 percent);
3. the plant which is needed for carrying out the method according to this invention does only comprise two tanks, whereas three tanks are needed for the known method;
4. the excess of piperazine used in the process according to this invention may be recovered and used again for preparing further amounts of the desired compound;
5. the single solvent used in the method according to this invention may be recovered and used again for preparing further amounts of the desired salt.

The salt of formula I is a pharmaceutical product which shows unexpected and substantial advantages, if compared to 1,2-diphenyl-4-butyl-3,5-dioxo pyrazolidine. Tests in vivo on animals and human beings have shown that the salt of the formula I is substantially less toxic than 1,2-diphenyl-4-butyl-3,5-dioxo pyrazolidine, whereas the tolerance of said salt is substantially better. Moreover, while administration of 1,2-diphenyl-4-butyl-3,5-dioxo pyrazolidine to human beings causes a substantial decrease of the excretion of electrolytes, it has been found that said excretion is normal when the salt of formula I is administered. Accordingly, the salt may be administered during a longer period and at higher doses, without the necessity of imposing a salt free or salt poor diet to the patient. Is has also been found that the salt of formula I acts much more quickly than the base pyrazolidine administered alone.

What I claim is:

1. A process for preparing the equimolecular salt of piperazine and 1,2-diphenyl-4-butyl-3,5-dioxo pyrazolidine, in which a solution of 1,2-diphenyl-4-butyl-3,5-dioxo pyrazolidine in an organic solvent selected from acetone, tetrahydrofuran, dioxane, toluene and the chlorinated aliphatic hydrocarbons of the formula $C_xH_yCl_z$, in which $x = 1, 2$ or $3$, $y = 0$ to $6$ inclusive and $z = 1$ to $6$ inclusive, is poured into a solution of an excess of piperazine in the same organic solvent, the obtained mixture is stirred and seed crystals of the desired equimolecular salt are added to the stirred reaction mixture when this mixture is at a temperature at which the seed crystals do not become dissolved in said mixture and at which no precipitation has been initiated in said mixture, the stirring of the reaction mixture being then continued until a precipitate is obtained, and recovering said precipitate.

2. A process according to claim 1, in which the organic solvent is selected among dioxane, tetrahydrofuran, toluene, dichloromethane, dichloroethane, chloroform and carbon tetrachloride.

3. A process according to claim 1 in which the precipitate is recovered by filtration, washed with hexane or light petroleum ether and dried.

* * * * *

UNITED STATES PATENT OFFICE
CERTIFICATE OF CORRECTION

Patent No. 3,976,646      Dated August 24, 1976

Inventor(s) Beaudet, Camille; Brussels, Belgium

It is certified that error appears in the above-identified patent and that said Letters Patent are hereby corrected as shown below:

In the Title page, the name of the Assignee should read -- Societe D'ETUDES ET DE REALISATIONS SCIENTIFIQUES EN ABREGE S.E.R.E.S.C.I. --.

Signed and Sealed this

Fourth Day of January 1977

[SEAL]

Attest:

RUTH C. MASON
*Attesting Officer*

C. MARSHALL DANN
*Commissioner of Patents and Trademarks*